United States Patent [19]

Martin et al.

[11] Patent Number: 5,607,387
[45] Date of Patent: Mar. 4, 1997

[54] ORTHOPEDIC SPLINT

[75] Inventors: James C. Martin, Baldwin; Randall S. Kilburn, Lawrence, both of Kans.; Robert L. Hamilton, Kansas City, Mo.; Mary J. Schmalz, Lawrence; Brian E. Palmer, Olathe, both of Kans.

[73] Assignee: M-Pact Worldwide Management Corporation, Eudora, Kans.

[21] Appl. No.: 389,220

[22] Filed: Feb. 15, 1995

[51] Int. Cl.⁶ ........................................ A61F 5/00
[52] U.S. Cl. ..................................... 602/6; 602/8
[58] Field of Search .................. 602/5, 6, 8, 9, 602/60, 63, 77, 62; 128/856, 877

[56] References Cited

U.S. PATENT DOCUMENTS

| | | |
|---|---|---|
| 3,923,049 | 12/1975 | Lauber et al. |
| 4,433,680 | 2/1984 | Yoon . |
| 4,628,917 | 12/1986 | Campagna, Jr. et al. |
| 4,748,974 | 6/1988 | Richter et al. |
| 4,770,299 | 9/1988 | Parker . |
| 4,869,046 | 9/1989 | Parker . |
| 4,893,617 | 1/1990 | Bartial et al. ............................. 602/8 |
| 4,899,738 | 2/1990 | Parker ...................................... 602/8 |
| 5,003,970 | 4/1991 | Parker et al. |
| 5,027,803 | 7/1991 | Scholz et al. .............................. 602/8 |
| 5,176,621 | 1/1993 | Schulz ....................................... 602/8 |
| 5,284,468 | 2/1994 | Nelson ................................... 602/8 X |
| 5,318,504 | 6/1994 | Edenbaum et al. ....................... 602/8 |
| 5,324,252 | 6/1994 | Libbey et al. .......................... 602/8 X |

OTHER PUBLICATIONS

Two-sided brochure of OCL Synthetic Custom Splinting System.
Brochure of Ortho–Glass entitled "It's a Clean Break from the Old Splinting Systems," dated 1991.

*Primary Examiner*—Richard J. Apley
*Assistant Examiner*—Kim M. Lee
*Attorney, Agent, or Firm*—Shook, Hardy & Bacon L.L.P.

[57] ABSTRACT

A splint product is used for forming a hard structure about a body portion. The product includes a substrate impregnated with a resin that hardens when exposed to water. A protective water-impervious envelope surrounds the substrate and shields the substrate from exposure to moisture in the atmosphere. An outer cushioning wrap surrounds the protective envelope and is for engaging the body portion. Prior to wetting of the splint product, the protective envelope is removed from its shielding position about the substrate so that the substrate remains inside the outer wrap. The outer wrap with the substrate therein is exposed to water and applied to an appropriate body portion about which it hardens.

11 Claims, 2 Drawing Sheets

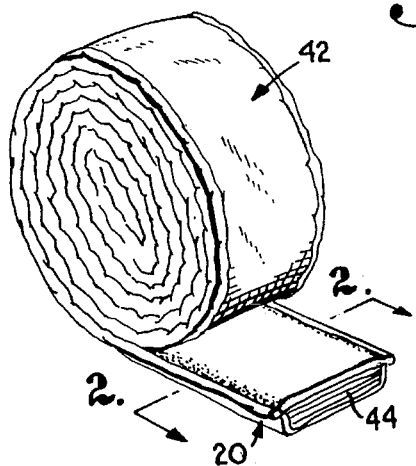
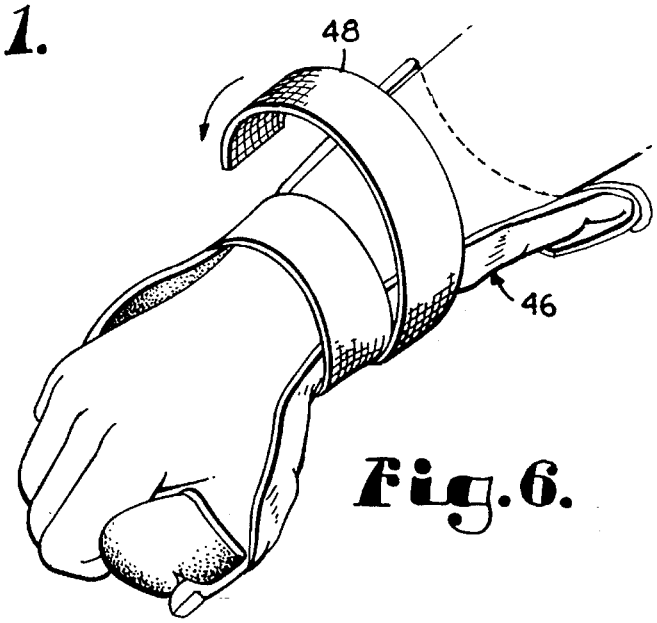
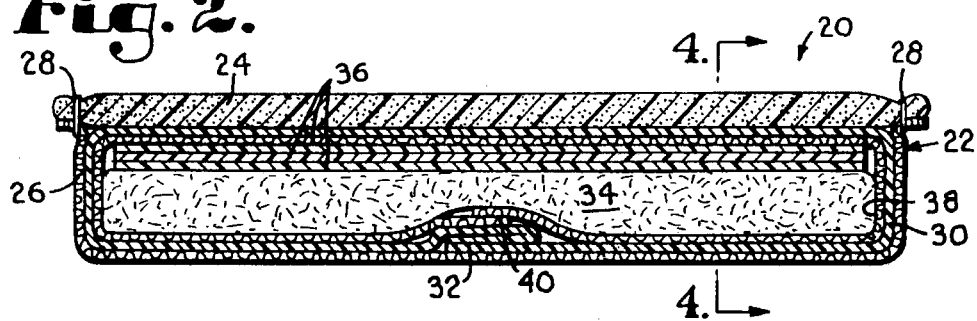
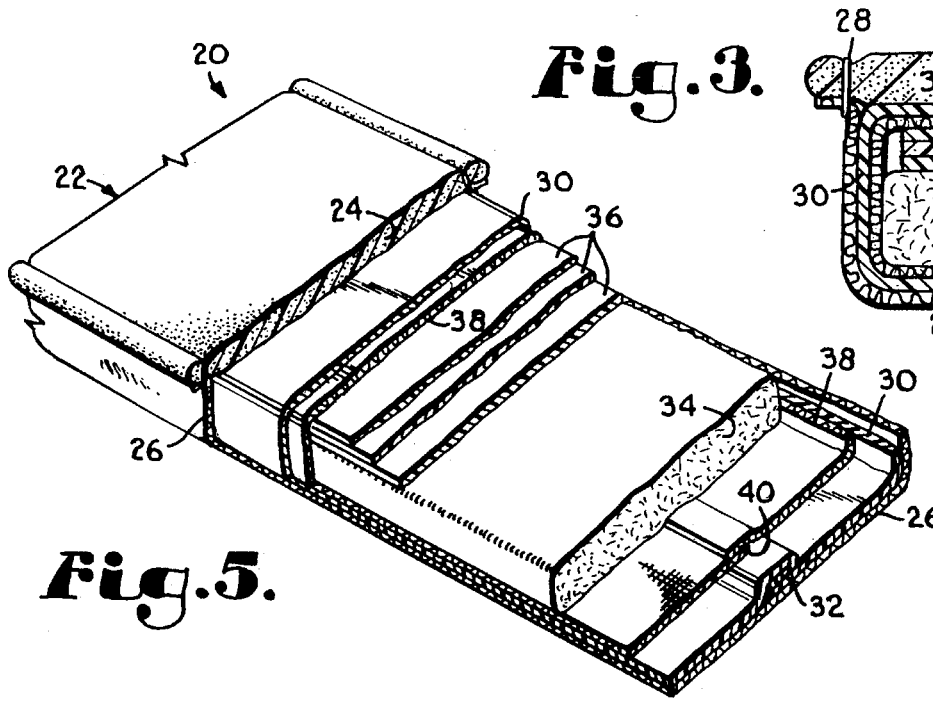

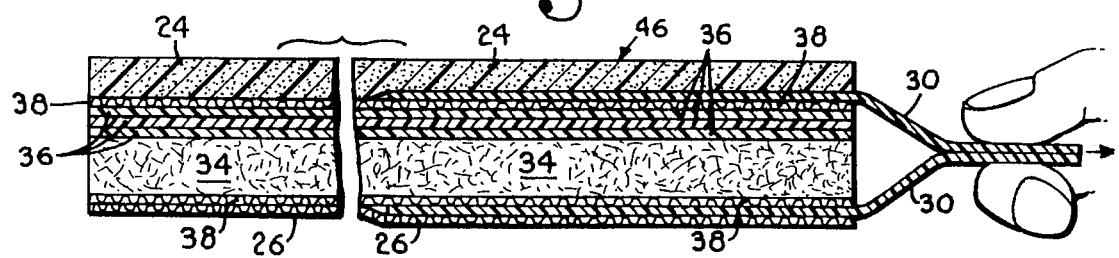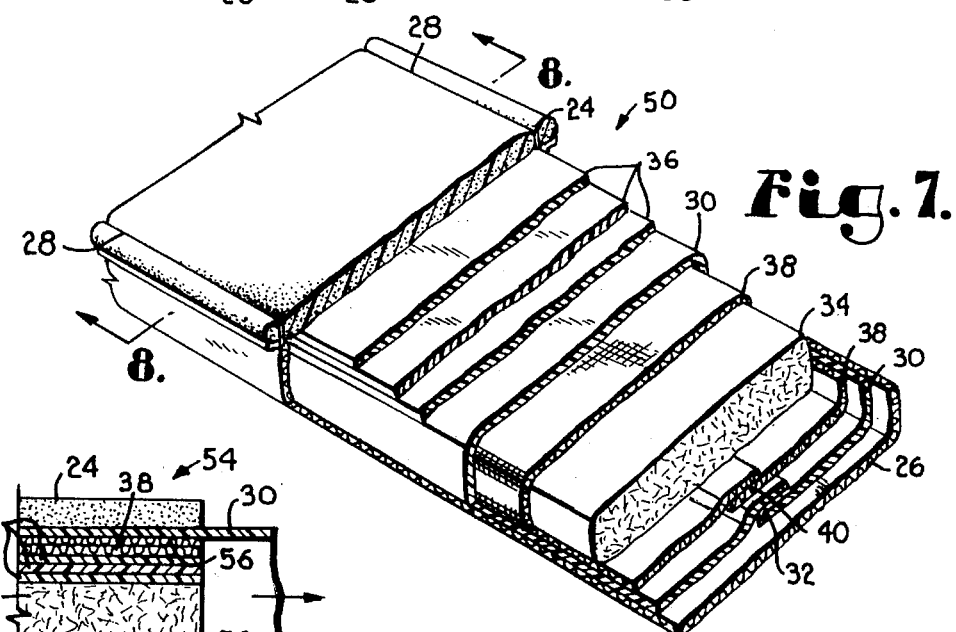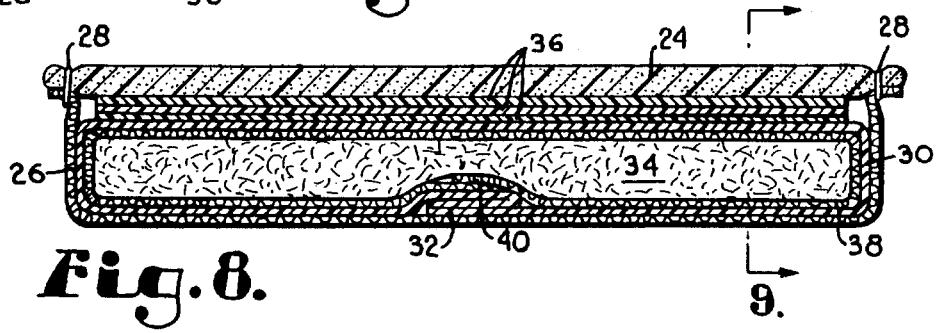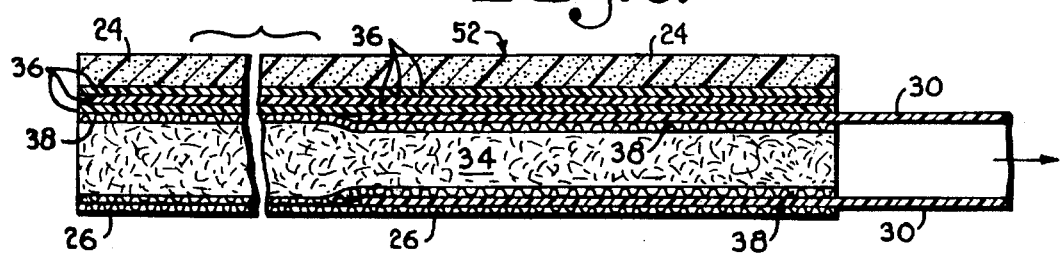

ORTHOPEDIC SPLINT

This invention relates in general to orthopedic splints and, more particularly, to water-activated orthopedic splints.

Many types of splints are typically available for orthopedic purposes such as to support and/or immobilize body portions to allow a broken bone or other injury to heal. Some of the more common types of splints include those made from plaster-of-paris, metals, high temperature plastics, low temperature plastics, and synthetic materials, such a polyurethane impregnated fiberglass.

Plaster-of-paris splints are widely utilized because of their low cost and their ability to conform to the contours of the underlying body portion. However, plaster also has a relatively low strength to weight ratio and the resulting splint tends to be very bulky and heavy in order to achieve the necessary strength, particularly when used to immobilize a person's leg.

Splints made from metal and high temperature plastics require the use of special tools for forming and shaping the splint prior to application. While splints resulting from such materials are considerably stronger and more durable than plaster splints, they are significantly more costly than plaster types. Because of their cost and the special tools required for their application, metal and high temperature plastic splints are generally unsuited for general usage.

The use of splints made from low temperature plastics is also limited by the need for a hot plate or tray of hot water to soften the plastic material prior to application. In addition to the inconveniences presented by such heating, the hot plastic presents a burn hazard to both the technician and the patient. Furthermore, the plastic material does not permit ventilation of the skin surface.

Synthetic splints typically include layers of fiberglass cloth coated with a water-activated polyurethane resin and enclosed within a padding material. Synthetic splints typically are lighter, more durable, and more water-resistant than plaster splints. However, the resin used in synthetic splints is usually very sensitive to minute amounts of moisture. More specifically, such a resin can be activated simply by exposure to moisture in the atmosphere over a period of time. Further, when the resin-impregnated fiberglass dries, it often has sharp edges or sharp needles extending from its edges. These sharp edges and needles can result in the surrounding materials being cut and even possible laceration of skin of the technician or patient. Also, when multiple layers of fiberglass are used and they dry, the layers often will delaminate from stress. Still further, the fiberglass cloth used does not allow the health care professional the proper "feel" when molding the splint. That is, the professional cannot adequately feel the bone structure of a body part through the fiberglass layers during application. This "feel" allows more accurate molding of the splint.

U.S. Pat. Nos. 4,770,299; 4,869,046; and 4,899,738 disclose a particular type of synthetic splint. More specifically, these patents disclose a splint product that is rolled into a coil and positioned in a dispensing box. The product includes an elongated outer packaging sleeve formed of a moisture-impervious material and heat sealed along opposite and parallel extending sides to form an elongated tube. A medical material is positioned within the sleeve and includes a substrate formed of a number of overlaid layers of woven or knitted fabric, such as fiberglass. The substrate is contained within a tubular wrapping formed of a soft, flexible non-woven fiber, such as polypropylene. This wrapping is disclosed as providing a cushioning protective layer between the skin of the patient and the substrate. The substrate is coated with a reactive system which remains stable when maintained in substantially moisture-free conditions but which hardens upon exposure to sufficient moisture to form a rigid, self-supporting structure. In use, a portion of the splint product is separated from the coil and the outer sleeve of the remaining coiled product is sealed. The outer sleeve is removed from the separated portion and the medical material is exposed to water and then applied to the particular body portion.

The splint product discussed in these patents is disadvantageous for numerous reasons. First, positioning of the polypropylene cushioning layer inside of the outer moisture-impervious sleeve may result in premature hardening of the substrate during storage. More specifically, the cushioning layer may absorb moisture from the atmosphere during manufacture of the product. When the cushioning layer is positioned in the outer sleeve adjacent the substrate, this absorbed moisture may, to a limited extent, activate the resin in the substrate. Additionally, after a portion of the product has been separated from the coil and before the outer sleeve can be re-sealed, the cushioning layer adjacent the open end of the coil is likely to absorb moisture from the atmosphere. Thus, after sealing the outer sleeve and during storage of the coil, the substrate adjacent to the sealed end typically will harden. Before a new portion of the coil can be used, this hardened end is typically cut off of the portion and discarded. Therefore, a substantial portion of the coil can be wasted because of the positioning of the cushioning layer inside of the outer envelope.

This splint product also can potentially cause irritation to a patient because of migration of resin vapor and resin particles into the cushioning layer that contacts the patient's body surface. More specifically, because the cushioning layer is positioned inside the outer moisture-impervious sleeve and adjacent to the substrate, resin particles and resin vapor can migrate into the cushioning layer while the splint coil is stored and sealed. Oftentimes, the type of resin used has the potential to irritate a skin surface if substantial amounts exist in the skin-contacting layer.

The splint product of these patents can also be difficult to seal because of the bulk of the materials located in the outer sleeve. The provision of the two parallel side seams of the outer sleeve increases the chance of moisture leakage through the seams. The edge positioning of the seams also increases the likelihood of damage to the seams due to them catching on surrounding structures. Also, because the moisture-impervious sleeve is the outer layer with no other surrounding layers, the chance of the sleeve being punctured or torn is increased.

Additionally, the utilization of woven fiberglass layers to form the substrate of these splint products can result in the hardened splint not having consistent strength in all directions. More specifically, each woven layer of the substrate has fibers extending in uniform predetermined directions. Therefore, after hardening of the substrate, the splint can be more susceptible to structural failure when forces are applied that do not align with the directions of the woven fibers.

A further disadvantage of the splint product disclosed in the patents is that the actual specific dimensions of the splint cannot be determined through the outer sleeve. Therefore, templates that are currently used by health care professionals to fashion specific splints oftentimes cannot be used with this concealed structure.

Another disadvantage of the splint product is that, when the fiberglass substrate dries, it often has sharp edges or sharp needles extending from its edges which can damage the splint or harm the splint wearer. These layers are also susceptible to delamination over time. Still further, because the substrate is completely surrounded by the cushioning layer, the health care professional may not have the proper "feel" when applying the splint.

Therefore, a splint product construction is needed which will overcome the disadvantages and shortcomings of the prior art discussed above.

Accordingly, a primary object of the present invention is to provide a water-activated splint product construction which minimizes the possibility that a substrate impregnated with a water-activated resin will be exposed to moisture during storage so that the product has an extended shelf life.

Another important object of the present invention is to provide a water-activated splint product construction wherein the foam body-engaging layer of the construction and the outwardly-facing layer of the construction are not inside the waterproof protective envelope of the construction during storage so that the vapors and particles of the resin do not penetrate the foam layer or outer layer during storage. Penetration of this type due to prolonged exposure during storage can potentially cause irritation of the body portion engaged by the splint product due to the characteristics of the resin used.

Another important object of the present invention is to prevent premature activation of the substrate during storage due to contact with moisture accumulated in the foam layer and outer layer, especially in a remaining portion of the product stored after a desired portion has been separated for use.

Another object of the present invention is to prevent waste of the splint product by positioning the foam layer and the outer layer of the construction outside of the waterproof protective envelope so that moisture accumulated in these layers cannot contact the substrate during storage of the unused portion of the product.

A still further object of the invention is to provide a protective envelope which can be easily and effectively sealed because it does not contain the foam layer and the outer layer.

Another object of this invention is to provide a protective envelope with only one seam positioned in the center of the envelope so as to decrease the chance of moisture penetration to the substrate, decrease the likelihood of damage to the seam, and decease the bulk of the splint product construction.

A further object is to provide a more puncture resistant splint construction because of the positioning of the foam layer and the outer layer around the protective envelope.

A still further object is to provide a splint construction which utilizes a single layer of non-woven material as the substrate. The random fibers of such a layer provide excellent conformability and numerous random intersections to increase the strength of the structure after hardening.

Another object is to provide a splint construction which can utilize layers of plaster-impregnated fabric in conjunction with the resin-impregnated substrate to increase the conformability and/or rigidity of the construction.

A further object is to provide a splint construction wherein the dimensions of the splint product can be clearly seen so that a template can be used to customize a splint.

These and other important aims and objects of the present invention will be further described or will become apparent from the following description and explanation of the drawings, wherein:

FIG. 1 is a top perspective view of a splint product embodying the principles of this invention and oriented in a dispensing roll;

FIG. 2 is a cross-sectional view taken generally along lines 2—2 of FIG. 1 and showing the construction of the splint product;

FIG. 3 is an enlarged fragmentary view of the left portion of FIG. 2;

FIG. 4 is a fragmentary cross-sectional view taken generally along lines 4—4 of FIG. 2 and showing the protective envelope being removed from a separated portion of the splint product;

FIG. 5 is a top perspective view of the splint product of FIG. 1, parts being broken away to reveal details of construction;

FIG. 6 is a diagrammatic view showing the application of a separated portion of the splint product to the arm of a patient;

FIG. 7 is a top perspective view of a splint product according to a further embodiment of this invention, parts being broken away to reveal details of construction;

FIG. 8 is an enlarged cross-sectional view taken generally along line 8—8 of FIG. 7;

FIG. 9 is a cross-sectional view taken generally along line 9—9 of FIG. 10 and showing the protective envelope being removed from a separated portion of the splint product; and FIG. 10 is a fragmentary cross-sectional view similar to the right-hand portion of FIG. 4, but showing an alternative construction of the protective envelope.

A splinting product embodying the principles of this invention is broadly designated in the drawings by the reference numeral 20. With reference to FIGS. 2–5, product 20 includes an elongated outer wrap 22 which includes an open cell foam layer 24 for engaging the body portion and an outer layer 26 formed of a suitable textile, such as cotton flannel. Foam layer 24 and outer layer 26 are stitched or bonded together along parallel seams 28 so that they form elongated outer wrap 22.

An elongated protective envelope 30 is positioned inside of wrap 22. Envelope 30 is preferably formed of aluminum foil, or any other suitable water-impervious material. The enclosure of envelope 30 is formed by connecting the edges of the foil along a single seam 32. Seam 32 is preferably formed by a thermal or ultrasonic welding process.

Disposed inside of envelope 30 is a substrate 34 which is impregnated with a water-activated resin. Substrate 34 is preferably formed of a single layer of non-woven material. The non-woven structure provides random fibers so that when the substrate is exposed to water and hardens, multiple random intersections between the fibers are formed, thus increasing the resistance of the hardened splint product to forces exerted in random directions. The non-woven structure also allows for conformability of the substrate about the body portion of the patient. One suitable type of substrate is A5 felt manufactured by Felters Company of Roebuck, South Carolina. The resin impregnated in substrate 34 is preferably a water-activated polyurethane resin such as is disclosed in U.S. Pat. No. 4,433,680, which is incorporated herein by reference.

Product 20 also has layers 36 of fabric impregnated with plaster-of-paris. Although three plaster layers 36 are shown in the figures, the number can be varied, but typically will not exceed five layers. Layers 36, when wetted and allowed to harden, rigidly conform to the body portion to which the splint is applied. Layers 36 are positioned adjacent to the side of substrate 34 that faces foam layer 24. Plaster layers 36 add an element of rigidity to the splint structure that cannot be achieved if only polyurethane impregnated substrate 34 is used. More specifically, although hardened substrate 34 provides great strength, because of the characteristics of polyurethane, the substrate will still bend and twist slightly when subjected to substantial forces. Further, because a limited number of plaster layers 36 are used, the splint maintains its lightweight characteristics.

Substrate 34 and layers 36 are surrounded by a layer 38 of a non-woven textile, for example, a textile made of polyester, such as a T-325 Stitchbond textile manufactured by the Titex Corporation of Spartansburg, South Carolina. Layer 38 is secured around the substrate and the plaster layers by attaching opposing edges of the layer at a seam 40 by a suitable process, for example, stitching or ultrasonic welding. The seam can be centrally located as depicted in the drawings or located along one side of the substrate. Layer 38 serves to maintain plaster layers 36 and substrate 34 in their respective orientation and further serves to facilitate removal of envelope 30 from the substrate and plastic layers, as will be more fully described below. Layer 38 also serves to inhibit the migration of resin particles or plaster particles to foam layer 24 during application of a splint to a body portion. Still further, layer 38 becomes imbedded with and around substrate 34 and plaster layers 36 after they harden. This accounts for a major portion of the strength of the splint.

Product 20 is preferably stored in and dispensed from a roll configuration 42, as shown in FIG. 1. During storage, substrate 34 and plaster layers 36 are protected from exposure to moisture in the atmosphere by sealing the open end 44 of protective envelope 30. This sealing can be done with a mechanical clamp or a suitable adhesive tape. It is important to note that only the envelope 30 need be sealed in order to guard against moisture contamination. Further, because body-engaging foam layer 24 and outer layer 26 are not positioned within the envelope, there is less bulk and, thus, easier closure.

After a portion 46 of the splinting product is separated from the roll, the roll is sealed against moisture in the manner described above. The section of protective envelope 30 in portion 46 is then removed by grasping the ends of the envelope and pulling the envelope away from the splint portion while maintaining textile layer 38, substrate 34, and plaster layers 36 within outer wrap 22, as demonstrated in FIG. 4. After envelope 30 has been removed from portion 46, only textile layer 38, substrate 34, and plaster layers 36 remain in wrap 22. This remaining structure is then submersed in water or otherwise wetted and applied and conformed to an appropriate body part as shown in FIG. 6. An elastic bandage 48 is then used to secure the damp portion 46 in place about the body portion. Substrate 34 and plaster layers 36 will then cure, thus resulting in hardening of the splint to immobilize the body portion. As described above, textile layer 38 becomes imbedded with the substrate and plaster layers after they harden to enhance the strength of the splint.

Because substrate 34 and plaster layers 36 are not in contact with foam layer 24 during storage, vapor from the resin in the substrate, resin particles and plaster particles are all prevented from migrating into the foam layer, such particles and vapors oftentimes causing skin irritation during application of the splint. Substrate 34 and plaster layers 36 are only exposed to foam layer 24 shortly before application of the splint, thus reducing substantially the possibility of any significant migration of vapor or particles.

Additionally, splint product 20 can be more effectively used because it is not necessary to remove and discard a small section of the roll adjacent the clamp or adhesive tape prior to cutting the desired length of splint. More specifically, because wrap 22 is positioned on the outside of protective envelope 30, moisture accumulated in the outer wrap cannot come into contact with the substrate as often happens in prior art splint products.

Further, the construction of product 20 reduces the possibility of moisture leakage during storage because protective envelope 30 has only one centrally disposed seam 32. This reduces the chances of leakage at the seam and further reduces the possibility of the seam being caught on surrounding structures during handling of the product. Further, positioning wrap 22 outside of envelope 30 adds an additional layer of protection to prevent puncturing of the envelope. An additional advantage of splinting product 20 is that it allows use of standard templates used to fashion splints for particular body parts because a medical professional can align the template with the actual dimensions of the finished splint instead of such dimensions being concealed within an outer envelope.

Splinting product 20 is constructed by first dipping substrate 34 in a suitable resin. The amount of resin applied to the substrate can be varied to customize the strength of the splint product for a particular application. The layers 36 of plaster impregnated fabric are then positioned on top of the substrate. Textile layer 38 is wrapped around the substrate and the plaster layers and sealed along seam 40 by stitching or ultrasonic welding. Aluminum foil is then wrapped around the textile layer and sealed along seam 32 by, for instance, thermal or adhesive welding so as to form protective envelope 30. Foam layer 24 and flannel layer 26 are then positioned about protective envelope 30 and stitched along parallel seams 28 to enclose the protective envelope and form wrap 22.

An alternative splinting product construction embodying the principles of this invention is shown in FIGS. 7–9 and broadly designated by the reference numeral 50. In the description of splinting product 50, parts similar to those of splinting product 20 are indicated with like reference numerals. Splinting product 50 differs from splinting product 20 in that plaster layers 36 are positioned outside of protective envelope 30 instead of adjacent to substrate 34. More specifically, textile layer 38 only surrounds substrate 34 and only the textile layer and the substrate are positioned within protective envelope 30. Plaster layers 36 are positioned between envelope 30 and body-engaging foam layer 24.

Splinting product 50 is used in the same manner as splinting product 20. That is, a portion of the product is separated from a storage roll and the end of the roll is then sealed by sealing the end of protective envelope 30. A separated portion 52 of product 50 is then readied for application by removing the section of protective envelope 30 contained in portion 52, as shown in FIG. 9. Envelope 30 is removed from portion 52 in the same manner as it is removed from portion 46. That is, envelope 30 is slid out of portion 52 so that the plaster layers, the substrate and the textile layer remain in outer wrap 22. Portion 52 is then submersed in water or otherwise wetted and applied to the body portion in the same manner as portion 46.

An alternative splinting product construction is shown in FIG. 10 and generally designated by the reference numeral 54. In the description of splinting product 54, parts similar to those of splinting product 20 are indicated with like reference numerals. Product 54 has an arrangement similar to that of product 20, except that it has an additional inner protective envelope 56 made of a water soluble plastic material, preferably polyvinyl alcohol. Plastic envelope 56 is located directly inside of foil envelope 30 and completely surrounds the substrate, the plaster layers and the textile layer. Plastic envelope 56 enhances removal of foil envelope 30 by preventing the textile layer from sticking to foil envelope due to resin migrating through the textile layer from the substrate. Plastic envelope 56 remains around the substrate, the plaster layers and the textile layer after protective foil envelope 30 is removed, as shown in FIG. 10. Plastic envelope 56 is preferably formed with a single side seam located along one side of the substrate. Splinting product 54 is applied in the same manner as splinting products 20 and 50. Plastic envelope 56 dissolves as a result of product 54 being submersed in water. Although the plastic layer is depicted in FIG. 10 with a construction similar to product 20, the plastic envelope can be used in any of the splint constructions described herein.

It may be desirable in certain situations not to include any plaster layers 36 in the splint product construction. Thus, such a construction would be similar to the construction shown in FIGS. 7–9, except that the three plaster layers 36 would not be present. During storage, the outer surface of protective envelope 30 would be directly adjacent to foam layer 24. When applied to a body portion after removal of envelope 30, textile layer 38 will be directly adjacent foam layer 24. As is apparent, it is also possible to utilize a plastic layer, as described above, in such a construction.

Having described the invention, what is claimed is:

1. A splint product for forming a hard structure about a body portion comprising a unitary assembly of:
    a substrate impregnated with a resin that hardens when exposed to water;
    a protective moisture-impervious envelope surrounding said substrate and shielding said substrate from exposure to moisture in the atmosphere;
    an outer cushioning wrap surrounding said protective envelope and for engaging the body portion, and wherein, prior to wetting of the splint product, said protective envelope is removed from its shielding position about the substrate so that the substrate remains inside the outer wrap, said outer wrap with said substrate therein being exposed to water and applied to an appropriate body portion about which it hardens.

2. The splint product of claim 1 wherein the splint product is in the form of an elongated strip so that a desired portion of the product can be separated from the remainder of the product and utilized as a splint, said substrate of the remainder being protected from atmospheric moisture for future use by sealing the open end of said protective envelope.

3. The splint material of claim 1 wherein said substrate is surrounded by a layer of non-woven textile which inhibits migration of said resin to said outer wrap and provides added structural support to the hardened splint product, said non-woven textile layer and said substrate being surrounded by said protective envelope.

4. The splint product of claim 1 wherein said substrate is made of a single layer of a non-woven material so that the random fibers of the material can be easily molded to the body portion and provide numerous randomly-directed intersections that are solidified during curing to provide strength.

5. The splint product of claim 1 wherein said outer wrap is made of a layer of open cell foam for contacting the body portion and a layer of cotton flannel opposite to said foam layer that does not contact the body portion.

6. The splint product of claim 1 further comprising at least one layer of a fabric impregnated with plaster, said plaster layer hardening after being exposed to water and conforming to the body portion, said plaster layer positioned inside of said outer wrap and wetted at the same time as said outer wrap and said substrate.

7. A splint product for forming a hard structure about a body portion comprising:
    a substrate impregnated with a resin that hardens when exposed to water;
    a protective moisture-impervious envelope surrounding said substrate and shielding said substrate from exposure to moisture in the atmosphere;
    an outer cushioning wrap surrounding said protective envelope and for engaging the body portion, and wherein prior to wetting of the splint product, said protective envelope is removed from its shielding position about the substrate so that the substrate remains inside the outer wrap, said outer wrap with said substrate therein being exposed to water and applied to an appropriate body portion about which it hardens; and
    at least one layer of a fabric impregnated with plaster, said plaster layer hardening after being exposed to water and conforming to the body portion, said plaster layer positioned inside of said outer wrap and wetted at the same time as said outer wrap and said substrate, wherein said plaster layer is positioned outside of said protective envelope.

8. The splint product of claim 6 wherein said plaster layer is positioned inside of said protective envelope.

9. The splint product of claim 1 wherein said protective envelope is made of an moisture-impervious foil, said protective envelope formed with only one centrally-positioned seam so that the bulk of the stored splint product is reduced and the chance of seam failure is reduced.

10. The splint product of claim 9 further comprising a layer of relatively slick plastic material disposed directly inside of said protective envelope, said plastic layer inhibiting sticking and catching of the structures surrounded by said protective envelope, said plastic layer surrounding said substrate prior to and subsequent to removal of said protective envelope from said shielding position.

11. The splint product of claim 1 wherein said resin is a water-activated polyurethane.

* * * * *